United States Patent
Luciano et al.

(10) Patent No.: US 10,096,096 B2
(45) Date of Patent: *Oct. 9, 2018

(54) AUTOMATIC ALIGNMENT OF A CONTRAST ENHANCEMENT SYSTEM

(71) Applicant: AccuVein, Inc., Cold Spring Harbor, NY (US)

(72) Inventors: Vincent Luciano, Shoreham, NY (US); Fred Wood, Medford, NY (US)

(73) Assignee: AccuVein, Inc., Cold Spring Harbor, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/665,504

(22) Filed: Aug. 1, 2017

(65) Prior Publication Data
US 2018/0012343 A1    Jan. 11, 2018

Related U.S. Application Data

(63) Continuation of application No. 15/226,027, filed on Aug. 2, 2016, now Pat. No. 9,760,982, which is a continuation of application No. 14/196,172, filed on Mar. 4, 2014, now Pat. No. 9,430,819, which is a
(Continued)

(51) Int. Cl.
| | |
|---|---|
| *G06T 5/00* | (2006.01) |
| *H04N 9/31* | (2006.01) |
| *A61B 5/00* | (2006.01) |
| *H04N 5/33* | (2006.01) |

(52) U.S. Cl.
CPC ............ *G06T 5/009* (2013.01); *A61B 5/0059* (2013.01); *A61B 5/0082* (2013.01); *A61B 5/489* (2013.01); *H04N 5/33* (2013.01); *H04N 9/3176* (2013.01); *H04N 9/3185* (2013.01); *H04N 9/3194* (2013.01)

(58) Field of Classification Search
CPC ....... A61B 5/0059; A61B 5/489; G06T 5/009; H04N 5/33; H04N 9/3176
USPC .... 348/77, 162, 164, 135, 136, 137; 345/32; 600/473; 353/10
See application file for complete search history.

(56) References Cited

U.S. PATENT DOCUMENTS

| | | | |
|---|---|---|---|
| 3,136,310 A | 6/1964 | Meltzer | |
| 3,349,762 A | 10/1967 | Kapany | |
| 3,511,227 A | 5/1970 | Johnson | |

(Continued)

FOREIGN PATENT DOCUMENTS

| | | |
|---|---|---|
| FR | 2289149 | 5/1976 |
| GB | 1298707 | 12/1972 |

(Continued)

OTHER PUBLICATIONS

Wiklof, Chris, "Display Technology Spawns Laser Camera," LaserFocusWorld, Dec. 1, 2004, vol. 40, Issue 12, PennWell Corp., USA.

(Continued)

*Primary Examiner* — Thai Tran
*Assistant Examiner* — Stephen Smith
(74) *Attorney, Agent, or Firm* — Thomas A. O'Rourke; Bodner & O'Rourke, LLP

(57) ABSTRACT

An apparatus and method for insuring the proper alignment of a detected vein pattern and a projected vein pattern are disclosed. The apparatus enhances the visual appearance of veins so that an error that can lead to improper patient care or injury can be avoided.

10 Claims, 3 Drawing Sheets

Related U.S. Application Data continuation of application No. 12/215,713, filed on Jun. 27, 2008, now Pat. No. 8,730,321.

(60) Provisional application No. 60/937,618, filed on Jun. 28, 2007.

(56) References Cited

U.S. PATENT DOCUMENTS

| | | |
|---|---|---|
| 3,527,932 A | 9/1970 | Thomas |
| 3,818,129 A | 6/1974 | Yamamoto |
| 3,984,629 A | 10/1976 | Gorog |
| 4,030,209 A | 6/1977 | Dreidling |
| 4,057,784 A | 11/1977 | Tafoya |
| 4,109,647 A | 8/1978 | Stern |
| 4,162,405 A | 7/1979 | Chance |
| 4,182,322 A | 1/1980 | Miller |
| 4,185,808 A | 1/1980 | Donohoe et al. |
| 4,213,678 A | 7/1980 | Pomerantzeff |
| 4,265,227 A | 5/1981 | Ruge |
| 4,312,357 A | 1/1982 | Andersson et al. |
| 4,315,318 A | 2/1982 | Kato |
| 4,321,930 A | 3/1982 | Jobsis et al. |
| 4,393,366 A | 7/1983 | Hill |
| 4,495,949 A | 1/1985 | Stoller |
| 4,502,075 A | 2/1985 | DeForest et al. |
| 4,510,938 A | 4/1985 | Jobsis |
| 4,536,790 A | 8/1985 | Kruger |
| 4,565,968 A | 1/1986 | Macovski |
| 4,567,896 A | 2/1986 | Barnea |
| 4,576,175 A | 3/1986 | Epstein |
| 4,586,190 A | 4/1986 | Tsuji |
| 4,590,948 A | 5/1986 | Nilsson |
| 4,596,254 A | 6/1986 | Adrian |
| 4,619,249 A | 10/1986 | Landry |
| 4,669,467 A | 6/1987 | Willet |
| 4,697,147 A | 9/1987 | Moran |
| 4,699,149 A | 10/1987 | Rice |
| 4,703,758 A | 11/1987 | Omura |
| 4,766,299 A | 8/1988 | Tierney et al. |
| 4,771,308 A | 9/1988 | Tejima et al. |
| 4,780,919 A | 11/1988 | Harrison |
| 4,799,103 A | 1/1989 | Mucherheide |
| 4,817,622 A | 4/1989 | Pennypacker et al. |
| 4,846,183 A | 7/1989 | Martin |
| 4,861,973 A | 8/1989 | Hellekson et al. |
| 4,862,894 A | 9/1989 | Fujii |
| 4,899,756 A | 2/1990 | Sonek |
| 4,901,019 A | 2/1990 | Wedeen |
| 4,926,867 A | 5/1990 | Kanda |
| RE33,234 E | 6/1990 | Landry |
| 4,938,205 A | 7/1990 | Nudelman |
| 5,074,642 A | 12/1991 | Hicks |
| 5,088,493 A | 2/1992 | Giannini |
| 5,103,497 A | 4/1992 | Hicks |
| 5,146,923 A | 9/1992 | Dhawan |
| 5,174,298 A | 12/1992 | Dolfi |
| 5,184,188 A | 2/1993 | Bull |
| 5,214,458 A | 5/1993 | Kanai |
| 5,222,495 A | 6/1993 | Clarke |
| 5,261,581 A | 11/1993 | Harden |
| 5,293,873 A | 3/1994 | Fang |
| 5,339,817 A | 8/1994 | Nilsson |
| 5,371,347 A | 12/1994 | Plesko |
| 5,406,070 A | 4/1995 | Edgar et al. |
| 5,418,546 A | 5/1995 | Nakagakiuchi et al. |
| 5,423,091 A | 6/1995 | Lange |
| 5,436,655 A | 7/1995 | Hiyama |
| D362,910 S | 10/1995 | Creaghan |
| 5,455,157 A | 10/1995 | Hinzpeter et al. |
| 5,494,032 A | 2/1996 | Robinson |
| 5,497,769 A | 3/1996 | Gratton |
| 5,504,316 A | 4/1996 | Bridgelall et al. |
| 5,519,208 A | 5/1996 | Esparza et al. |
| 5,541,820 A | 7/1996 | McLaughlin |
| 5,542,421 A | 8/1996 | Erdman |
| 5,598,842 A | 2/1997 | Ishihara et al. |
| 5,603,328 A | 2/1997 | Zucker et al. |
| 5,608,210 A | 3/1997 | Esparza et al. |
| 5,610,387 A | 3/1997 | Bard et al. |
| 5,625,458 A | 4/1997 | Alfano |
| 5,631,976 A | 5/1997 | Bolle et al. |
| 5,655,530 A | 8/1997 | Messerschmidt |
| 5,678,555 A | 10/1997 | O'Connell |
| 5,716,796 A | 2/1998 | Bull |
| 5,719,399 A | 2/1998 | Alfano et al. |
| 5,747,789 A | 5/1998 | Godik |
| 5,756,981 A | 5/1998 | Roustaei et al. |
| 5,758,650 A | 6/1998 | Miller |
| 5,772,593 A | 6/1998 | Hakamata |
| 5,787,185 A | 7/1998 | Clayden |
| 5,814,040 A | 9/1998 | Nelson |
| 5,836,877 A | 11/1998 | Zavislan |
| 5,847,394 A | 12/1998 | Alfano et al. |
| 5,860,967 A | 1/1999 | Zavislan et al. |
| 5,929,443 A | 7/1999 | Alfano et al. |
| 5,946,220 A | 8/1999 | Lemelson |
| 5,947,906 A | 9/1999 | Dawson, Jr. et al. |
| 5,966,204 A | 10/1999 | Abe |
| 5,966,230 A | 10/1999 | Swartz et al. |
| 5,969,754 A | 10/1999 | Zeman |
| 5,982,553 A | 11/1999 | Bloom et al. |
| 5,988,817 A | 11/1999 | Mizushima et al. |
| 5,995,856 A | 11/1999 | Manheimer et al. |
| 5,995,866 A | 11/1999 | Lemelson |
| 6,006,126 A | 12/1999 | Cosman |
| 6,032,070 A | 2/2000 | Flock et al. |
| 6,056,692 A | 5/2000 | Schwartz |
| 6,061,583 A | 5/2000 | Ishihara et al. |
| 6,101,036 A | 8/2000 | Bloom |
| 6,122,042 A | 9/2000 | Wunderman |
| 6,132,379 A | 10/2000 | Patacsil |
| 6,135,599 A | 10/2000 | Fang |
| 6,141,985 A | 11/2000 | Cluzeau et al. |
| 6,142,650 A | 11/2000 | Brown et al. |
| 6,149,061 A | 11/2000 | Massieu et al. |
| 6,149,644 A | 11/2000 | Xie |
| 6,171,301 B1 | 1/2001 | Nelson |
| 6,178,340 B1 | 1/2001 | Svetliza |
| 6,230,046 B1 | 5/2001 | Crane et al. |
| 6,240,309 B1 | 5/2001 | Yamashita |
| 6,251,073 B1 | 6/2001 | Imran et al. |
| 6,263,227 B1 | 7/2001 | Boggett et al. |
| 6,301,375 B1 | 10/2001 | Choi |
| 6,305,804 B1 | 10/2001 | Rice |
| 6,314,311 B1 | 11/2001 | Williams et al. |
| 6,334,850 B1 | 1/2002 | Amano et al. |
| 6,353,753 B1 | 3/2002 | Flock |
| 6,424,858 B1 | 7/2002 | Williams |
| 6,436,655 B1 | 8/2002 | Bull |
| 6,438,396 B1 | 8/2002 | Cook et al. |
| 6,463,309 B1 | 10/2002 | Ilia |
| 6,464,646 B1 | 10/2002 | Shalom et al. |
| 6,523,955 B1 | 2/2003 | Eberl |
| 6,542,246 B1 | 4/2003 | Toida |
| 6,556,854 B1 | 4/2003 | Sato et al. |
| 6,556,858 B1 | 4/2003 | Zeman |
| 6,599,247 B1 | 7/2003 | Stetten |
| 6,631,286 B2 | 10/2003 | Pfeiffer |
| 6,648,227 B2 | 11/2003 | Swartz et al. |
| 6,650,916 B2 | 11/2003 | Cook et al. |
| 6,689,075 B2 | 2/2004 | West |
| 6,690,964 B2 | 2/2004 | Bieger et al. |
| 6,702,749 B2 | 3/2004 | Paladini et al. |
| 6,719,257 B1 | 4/2004 | Greene et al. |
| 6,755,789 B2 | 6/2004 | Stringer |
| 6,777,199 B2 | 8/2004 | Bull |
| 6,782,161 B2 | 9/2004 | Barolet et al. |
| 6,845,190 B1 | 1/2005 | Smithwick |
| 6,882,875 B1 | 4/2005 | Crowley |
| 6,889,075 B2 | 5/2005 | Marchitto et al. |
| 6,913,202 B2 | 7/2005 | Tsikos et al. |
| 6,923,762 B1 | 8/2005 | Creaghan |
| 6,980,852 B2 | 12/2005 | Jersey-Wiluhn et al. |
| 7,092,087 B2 | 8/2006 | Kumar |

(56) References Cited

U.S. PATENT DOCUMENTS

| | | | |
|---|---|---|---|
| 7,113,817 B1 | 9/2006 | Winchester | |
| 7,158,660 B2 | 1/2007 | Gee et al. | |
| 7,158,859 B2 | 1/2007 | Wang | |
| 7,204,424 B2 | 4/2007 | Yavid et al. | |
| 7,225,005 B2 | 5/2007 | Kaufman et al. | |
| 7,227,611 B2 | 6/2007 | Hull et al. | |
| 7,239,909 B2 | 7/2007 | Zeman | |
| 7,247,832 B2 | 7/2007 | Webb | |
| 7,280,860 B2 | 10/2007 | Ikeda et al. | |
| 7,283,181 B2 | 10/2007 | Allen | |
| 7,302,174 B2 | 11/2007 | Tan et al. | |
| 7,333,213 B2 | 2/2008 | Kempe | |
| D566,283 S | 4/2008 | Brafford et al. | |
| 7,359,531 B2 | 4/2008 | Endoh et al. | |
| 7,376,456 B2 | 5/2008 | Marshik-Geurts | |
| 7,428,997 B2 | 9/2008 | Wiklof et al. | |
| 7,431,695 B1 | 10/2008 | Creaghan | |
| 7,448,995 B2 | 11/2008 | Wiklof et al. | |
| 7,532,746 B2 | 5/2009 | Marcotte et al. | |
| 7,545,837 B2 | 6/2009 | Oka | |
| 7,559,895 B2 | 7/2009 | Stetten | |
| 7,579,592 B2 | 8/2009 | Kaushal | |
| 7,608,057 B2 | 10/2009 | Woehr et al. | |
| 7,699,776 B2 | 4/2010 | Walker et al. | |
| 7,708,695 B2 | 5/2010 | Akkermans | |
| 7,792,334 B2 | 9/2010 | Cohen | |
| 7,846,103 B2 | 12/2010 | Cannon, Jr. | |
| 7,904,138 B2 | 3/2011 | Goldman | |
| 7,904,139 B2 | 3/2011 | Chance | |
| 7,925,332 B2 | 4/2011 | Crane et al. | |
| 7,966,051 B2 | 6/2011 | Xie | |
| 8,032,205 B2 | 10/2011 | Muliani | |
| 8,078,263 B2 | 12/2011 | Zeman et al. | |
| 8,187,189 B2 | 5/2012 | Jung et al. | |
| 8,199,189 B2 | 6/2012 | Kagenow et al. | |
| 8,320,998 B2 | 11/2012 | Sato | |
| 8,336,839 B2 | 12/2012 | Boccoleri | |
| 8,364,246 B2 | 1/2013 | Thierman | |
| 8,467,855 B2 | 6/2013 | Yasui | |
| 8,494,616 B2 | 7/2013 | Zeman | |
| 8,498,694 B2 | 7/2013 | McGuire, Jr. et al. | |
| 8,509,495 B2 | 8/2013 | Xu et al. | |
| 8,548,572 B2 | 10/2013 | Crane et al. | |
| 8,630,465 B2 | 1/2014 | Wieringa | |
| 8,649,848 B2 | 2/2014 | Crane et al. | |
| 2001/0006426 A1 | 7/2001 | Son | |
| 2001/0056237 A1 | 12/2001 | Cane | |
| 2002/0016533 A1 | 2/2002 | Marchitto | |
| 2002/0118338 A1 | 8/2002 | Kohayakawa | |
| 2002/0188203 A1 | 12/2002 | Smith | |
| 2003/0018271 A1 | 1/2003 | Kimble | |
| 2003/0052105 A1 | 3/2003 | Nagano | |
| 2003/0120154 A1 | 6/2003 | Sauer | |
| 2003/0125629 A1 | 7/2003 | Ustuner | |
| 2003/0156260 A1 | 8/2003 | Putilin | |
| 2004/0015158 A1 | 1/2004 | Chen et al. | |
| 2004/0022421 A1 | 2/2004 | Endoh et al. | |
| 2004/0046031 A1 | 3/2004 | Knowles et al. | |
| 2004/0171923 A1 | 9/2004 | Kalafut et al. | |
| 2004/0222301 A1 | 11/2004 | Willins et al. | |
| 2005/0017924 A1 | 1/2005 | Utt et al. | |
| 2005/0033145 A1 | 2/2005 | Graham et al. | |
| 2005/0043596 A1 | 2/2005 | Chance | |
| 2005/0047134 A1 | 3/2005 | Mueller et al. | |
| 2005/0085802 A1 | 4/2005 | Gruzdev | |
| 2005/0113650 A1 | 5/2005 | Pacione et al. | |
| 2005/0131291 A1 | 6/2005 | Floyd et al. | |
| 2005/0135102 A1 | 6/2005 | Gardiner et al. | |
| 2005/0141069 A1 | 6/2005 | Wood et al. | |
| 2005/0143662 A1 | 6/2005 | Marchitto et al. | |
| 2005/0146765 A1 | 7/2005 | Turner | |
| 2005/0154303 A1 | 7/2005 | Walker | |
| 2005/0157939 A1 | 7/2005 | Arsenault et al. | |
| 2005/0161051 A1 | 7/2005 | Pankratov et al. | |
| 2005/0168980 A1 | 8/2005 | Dryden et al. | |
| 2005/0174777 A1 | 8/2005 | Cooper et al. | |
| 2005/0175048 A1 | 8/2005 | Stern et al. | |
| 2005/0187477 A1 | 8/2005 | Serov | |
| 2005/0215875 A1 | 9/2005 | Khou | |
| 2005/0265586 A1 | 12/2005 | Rowe et al. | |
| 2005/0281445 A1 | 12/2005 | Marcotte et al. | |
| 2006/0007134 A1 | 1/2006 | Ting | |
| 2006/0020212 A1 | 1/2006 | Xu | |
| 2006/0025679 A1 | 2/2006 | Viswanathan et al. | |
| 2006/0052690 A1 | 3/2006 | Sirohey et al. | |
| 2006/0081252 A1 | 4/2006 | Wood | |
| 2006/0100523 A1 | 5/2006 | Ogle | |
| 2006/0103811 A1 | 5/2006 | May et al. | |
| 2006/0122515 A1 | 6/2006 | Zeman | |
| 2006/0129037 A1 | 6/2006 | Kaufman et al. | |
| 2006/0129038 A1 | 6/2006 | Zelenchuk et al. | |
| 2006/0151449 A1 | 7/2006 | Warner | |
| 2006/0173351 A1 | 8/2006 | Marcotte et al. | |
| 2006/0184040 A1 | 8/2006 | Keller et al. | |
| 2006/0206027 A1 | 9/2006 | Malone | |
| 2006/0232660 A1 | 10/2006 | Nakajima et al. | |
| 2006/0253010 A1 | 11/2006 | Brady et al. | |
| 2006/0271028 A1 | 11/2006 | Altshuler et al. | |
| 2007/0016079 A1 | 1/2007 | Freeman et al. | |
| 2007/0070302 A1 | 3/2007 | Govorkov | |
| 2007/0115435 A1 | 5/2007 | Rosendaal | |
| 2007/0176851 A1 | 8/2007 | Wiley | |
| 2008/0045841 A1 | 2/2008 | Wood et al. | |
| 2008/0147147 A1 | 6/2008 | Griffiths et al. | |
| 2008/0194930 A1 | 8/2008 | Harris et al. | |
| 2009/0018414 A1 | 1/2009 | Toofan | |
| 2009/0171205 A1 | 7/2009 | Kharin | |
| 2010/0051808 A1 | 3/2010 | Zeman et al. | |
| 2010/0061598 A1 | 3/2010 | Seo | |
| 2010/0087787 A1 | 4/2010 | Woehr et al. | |
| 2010/0177184 A1 | 7/2010 | Berryhill et al. | |
| 2010/0312120 A1 | 12/2010 | Meier | |
| 2014/0039309 A1 | 2/2014 | Harris et al. | |
| 2014/0046291 A1 | 2/2014 | Harris et al. | |

FOREIGN PATENT DOCUMENTS

| | | |
|---|---|---|
| GB | 1507329 | 4/1976 |
| JP | S60-108043 A | 6/1985 |
| JP | 04-042944 | 2/1992 |
| JP | 07-255847 | 10/1995 |
| JP | 08023501 A | 1/1996 |
| JP | 08-164123 | 6/1996 |
| JP | 2000/316866 A | 11/2000 |
| JP | 2002 328428 A | 11/2002 |
| JP | 2002/345953 A | 12/2002 |
| JP | 2004 237051 | 8/2004 |
| JP | 2004/329786 A | 11/2004 |
| KR | 2003/0020152 A | 11/2004 |
| WO | WO 1994 22370 | 10/1994 |
| WO | WO 1996 39925 | 12/1996 |
| WO | WO 9826583 | 6/1998 |
| WO | WO 99/48420 | 9/1999 |
| WO | WO 2001 82786 | 11/2001 |
| WO | WO 2003 009750 | 2/2003 |
| WO | WO 2005/053773 | 6/2005 |
| WO | WO 2007078447 | 7/2007 |

OTHER PUBLICATIONS

Nikbin, Darius, "IPMS Targets Colour Laser Projectors," Optics & Laser Europe, Mar. 2006, Issue 137, p. 11.
http://sciencegeekgirl.wordpress.com/category/science-myths/page/2/Myth 7: Blood is Blue.
http://www.exploratorium.edu/sports/hnds_up/hands6.html "Hands Up! To Do & Notice: Getting the Feel of Your Hand".
http://www.wikihow.com/See-Blood-Veins-in-Your-Hand-With-a-Flashlight "How to See Blood Veins in Your Hand With a Flashlight".

AUTOMATIC ALIGNMENT OF A CONTRAST ENHANCEMENT SYSTEM

CROSS REFERENCES TO RELATED APPLICATIONS

This application is a continuation of U.S. application Ser. No. 15/226,027, filed Aug. 2, 2016, which is a continuation of U.S. application Ser. No. 14/196,172, filed Mar. 4, 2014, now issued as U.S. Pat. No. 9,430,819, which is a continuation of U.S. application Ser. No. 12/215,713, filed Jun. 27, 2008, now issued as U.S. Pat. No. 8,730,321, which claims priority on U.S. Provisional Application Ser. No. 60/937,618, filed Jun. 28, 2007, all disclosures of which are incorporated herein by reference.

SUMMARY OF THE INVENTION

An apparatus and method for insuring the proper alignment of a detected vein pattern and a projected vein pattern in a apparatus that enhances the visual appearance of veins so that an error that can lead to improper patient care or injury can be avoided.

BACKGROUND OF THE INVENTION

It is known in the sat to use an apparatus to enhance the visual appearance of the veins and arteries in a patient to facilitate insertion of needles into those veins and arteries as well as other medical practices that require the identification of vein and artery locations. Such a system is described in U.S. Pat. Nos. 5,969,754 and 6,556,858 incorporated herein by reference as well as publication entitled "The Clinical Evaluation of Vein Contrast Enhancement". Luminetx is currently marketing such a device under the name "Veinviewer Imaging System" and information related thereto is available on their website, which is incorporated herein by reference.

The Luminetx Vein Contrast Enhancer (hereinafter referred to as LVCE) utilizes a light source for flooding the region to be enhanced with near infrared light generated by an array of LEDs. A CCD imager is then used to capture an image of the infrared light reflected off the patient. The resulting captured image is then digitally enhanced and then projected by a visible light projector onto the patient in a position that must be closely aligned with position of the captured image. The practitioner uses this projected image to determine the position in which to insert a needle. Should the image be misaligned, the patient can be injured.

DETAILED DESCRIPTION OF THE INVENTION

Figure 1:
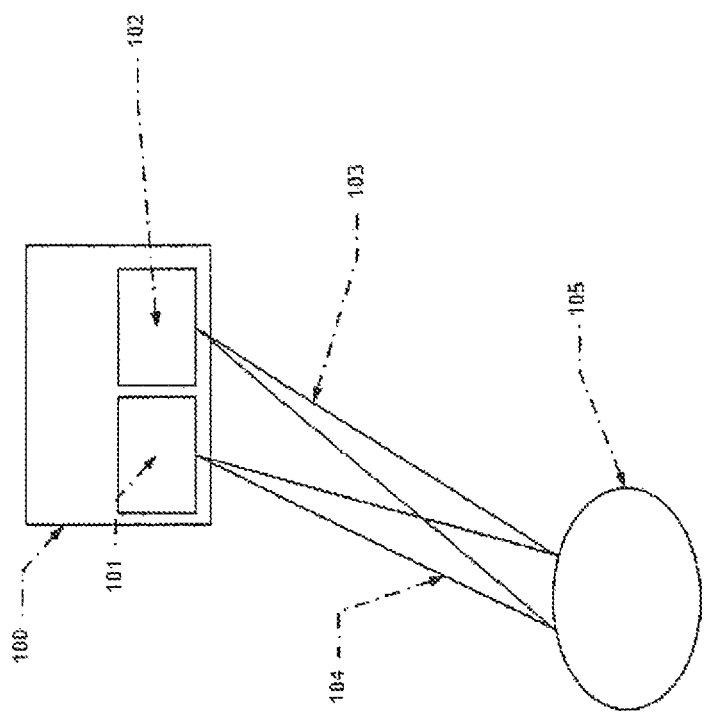
FIG. 1 shows an embodiment of a vein contrast enhancer.

As shown in FIG. 1, a typical embodiment of a vein contrast enhancer (VCE) 100 contains a camera 101 which is used to capture an image of a patient's body 105, a processing system (not shown) that enhances the image captured by the camera to highlight the positions of veins, and a projector 102 that shows an image of the enhanced vein pattern back onto the patient's body 105. Since the camera and projector are physically separate devices they reach the patient's body from different source points along different paths 103, 104. In some embodiments, the paths are made coaxial within the body of the VCE, however at some point the paths are separate since the devices (camera and projector) are physically separate devices. Since the purpose of VCE is to allow the practitioner to insert a needle into the highlighted vein, it is critically important that the projected image and the actual vein location be aligned. Typically this alignment is done as a separate step in the use of the VCE. A card with a known pattern is placed with the viewing/projecting field of the VCE. This card has a florescent material applied to it so that when it is struck by green light, it emits infrared light that can be seen by the camera. This image is used to align the VCE.

This invention describes methods for achieving this alignment without requiring the operator to take a separate step.

Figure 2:
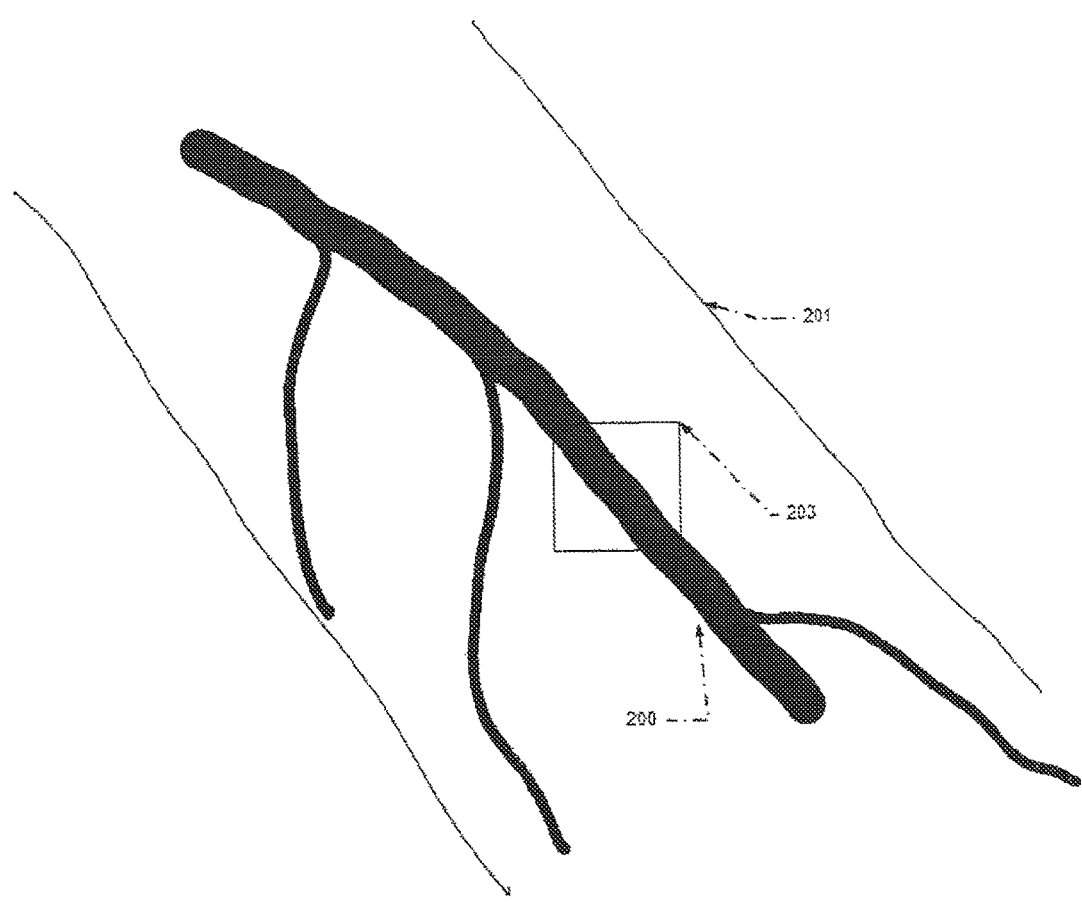
FIG. 2 is a representation of a patient's arm.
Figure 3:
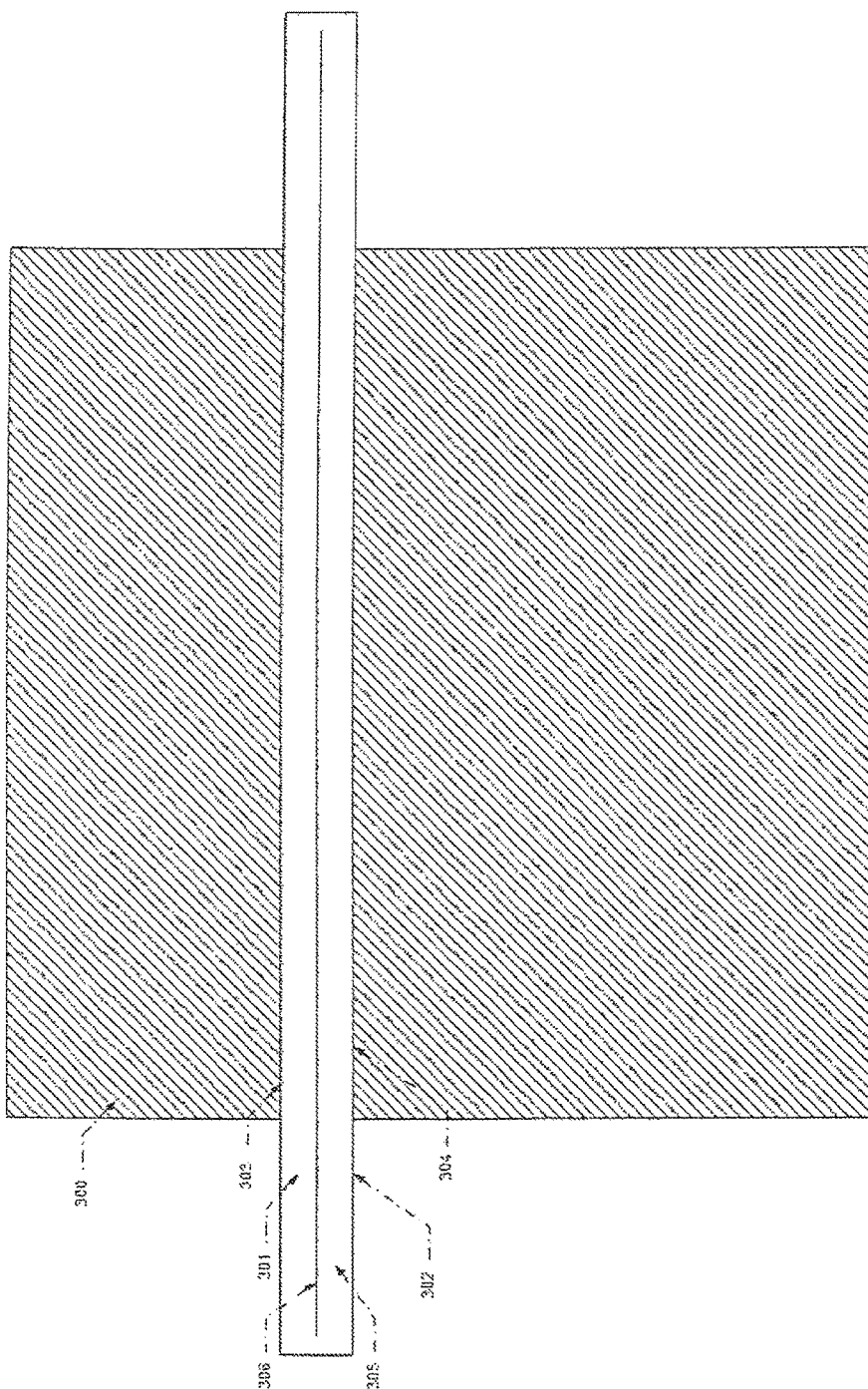
FIG. 3 shows an embodiment of a laser contrast enhancer

Referring to FIG. 2, a representation of the patient's arm 201 is shown along with several veins. A bounding box is shown around a single vein 200. In FIG. 3, a schematic representation of the bounded area of the single vein is shown 305. Typically, the enhancement image will light up the area around the vein and will be dark on the vein. When properly aligned, the bright part of the image 300 will have edges that properly align with the edges of the vein 303, 304. As previously described, the VCE will typically have an alignment mode wherein a known pattern, typically presented on an alignment card, will be placed in front of the VCE and an alignment will be performed. This alignment can either be automatically performed by the VCE or manually performed by the operator. The weakness of this kind of implementation is that is relies on the expectation that the alignment will be maintained over time. If the alignment should shift, patient injury can occur.

In a typical VCE, an infrared light source and a camera that is sensitive only to infrared light is used to detect the vein position. Furthermore, the projected image is often green in color to insure that the light from the projector is ignored since the camera is sensitive only to light near the infrared region. This selectivity can be implemented either with filters or with selectively sensitive camera elements.

Referring back to FIG. 3, in a typical LCE, the camera, by design, is blind to the projected light. In our invention, the camera is by design, able to selectively see the projected light. In a preferred embodiment, a multi-color capable projector is used. As usual, green is used to fill the area outside of the vein 300. That green projection goes to the edges of the vein position 303, 304 and the vein area itself is left dark. A camera that is sensitive to red and infrared light is used in this embodiment. In addition to the green fill, red lines are drawn at the edges of the veins 303, 304. Since the camera can see these red lines, the image enhancement software can look to see if the red lines are at the proper position and if needed automatic alignment can be performed. An alternative embodiment would be to paint a red line 306 down the middle of the vein position. An alternative embodiment would be to paint some pattern of red light over a desired portion of the vein.

Typically the cameras used in an LCE are monochrome and unable to discriminate between light of different wavelengths. Depending on the sensitivity of the camera and the brightness of the projector compared to the infrared flood lighting provided by the LCE, various techniques can be used to aid the camera in the detection of the red lines. One method is to simply look for the brightening caused by the addition of the red lines to the reflected infrared light. A second method is to periodically turn off the infrared lighting such that only ambient infrared and the projected red are seen by the camera. This can make it easier for the system to detect the red lines.

Although we've described the invention using red and green lights, various combinations of colors can be used. Red and infrared light are known in the art to be useful for vein detection. Any combinations of colors of shorter wavelengths can be used for projection and alignment images as long as the camera selected is properly selected or filtered to achieve the desired discrimination between wavelengths. Furthermore, while discrimination between projection, detection and alignment signals in the preferred embodiment has been described using different wavelengths to separate the signals, in an embodiment with less freedom of projected color, time division can be used where the projected image is shown most of the time and the alignment image is shown interspersed on a lower duty cycle basis. Properly implemented, the alignment image will be quite visible to the VCE's camera, but invisible to the operator of the VCE.

Projectors in VCEs can be either monochrome (e.g., projecting green only) or multicolor (e.g., projecting RGB). The advantage of a monochrome implementation is that since an array of single color LEDs can be used in place of white bulbs and a color wheel typically found in a multicolor projector the system can be of lower cost, generate less heat and have higher reliability. In such an embodiment, the time division scheme describe above would be appropriate. In this monochrome configuration, an alternative embodiment would be to add a smaller array of a second color of LEDs (i.e., red). Thus alignment array can be smaller than the projection, array in that it doesn't need to be visible to the operator, just to the camera. The projection LEDs and the alignment LEDs could then be time multiplexed and previously described.

We claim:

1. A vein imaging system comprising:
a light source configured to illuminate a field of view with a first wavelength of light comprising an infrared wavelength, to create an image contrast of one or more veins formed by differential amounts of absorption and reflection of said first wavelength of light by the one or more veins and surrounding tissue in the field of view;
an alignment card comprising a pattern, said alignment card configured to emit a second wavelength of light when positioned in the field of view and exposed to a third wavelength of light comprising a visible wavelength;
a camera configured to capture said image contrast of the one or more veins;
a projector configured to project said captured image contrast onto the field of view using said third wavelength of light;
wherein said camera is further configured to capture said second wavelength of light emitted by said alignment card, and to capture said visible light at said third wavelength reflected from said alignment card, said camera further configured to distinguish said third wavelength of light reflected by said alignment card, from said second wavelength of light emitted by said alignment card; and
an image processor configured to align said projection of said captured image contrast with said reflected image contrast, from said distinction between said captured reflection of said projected alignment card pattern at said third wavelength of light, and said captured emission from said alignment card pattern at said second wavelength.

2. The vein imaging system according to claim 1 wherein said alignment card comprises a fluorescent material.

3. The system according to claim 1 wherein said pattern of said alignment card comprises a known pattern.

4. The vein imaging system according to claim 1 wherein said third wavelength of light comprises a green wavelength of light.

5. The vein imaging system according to claim 4 wherein said green wavelength of light of said projected image contrast is projected onto the field of view outside of the one or more veins.

6. The vein imaging system according to claim 5 wherein said second wavelength of light comprises a red wavelength of light.

7. A method of ensuring proper aligning of a projected vein image with a captured vein image, said method comprising:
illuminating a field of view with a first wavelength of infrared light;
capturing said first wavelength of infrared light reflected from the field of view as an image contrast formed by differential absorption and reflection by veins and surrounding tissue therein;
forming an alignment card using a material configured for emitting a second wavelength of light when exposed to a visible light at a third wavelength;
positioning the alignment card in the field of view;
projecting the captured image contrast onto the field of view using the visible light at the third wavelength;
capturing; the second wavelength of light emitted by said alignment card, and the visible light at the third wavelength reflected from the field of view;
comparing a position of the alignment card in the captured reflection of the third wavelength, with the captured emission from the alignment card; and
aligning said projection of said captured image contrast according to a positional difference between said compared positions of the reflection of the projected alignment card and the emission from the alignment card.

8. The method according to claim 7, further comprising projecting the image contrast using green light for filling areas in the field of view being outside of the veins.

9. A vein imaging system comprising:
a light source configured to illuminate a field of view with a first wavelength of light comprising an infrared wavelength to create an image contrast of one or more veins, formed by differential amounts of absorption and reflection of said first wavelength of light by the one or more veins and surrounding tissue within the field of view;
an alignment card comprising a pattern, said alignment card configured to emit a second wavelength of light when positioned in the field of view and exposed to a third wavelength of light comprising a visible wavelength;
a camera configured to capture said image contrast of the one or more veins;
a projector configured to project said captured image contrast onto the field of view using said third wavelength of light;
wherein said camera is further configured to capture said second wavelength of light emitted by said alignment card, and to capture said visible light at said third wavelength reflected from said alignment card;
wherein said visible third wavelength of light and said infrared wavelength are alternately projected and illuminated, respectively; and an image processor configured to align said projection of said captured image contrast with said reflected image contrast, from a comparison of said captured reflection of said projected alignment card pattern at said third wavelength of light, with said captured emission from said alignment card pattern at said second wavelength.

10. The vein imaging system according to claim 9 wherein said projected visible third wavelength of light is projected at a higher duty cycle than said illumination of said infrared wavelength.

* * * * *